United States Patent
Ashida et al.

(10) Patent No.: US 8,735,442 B2
(45) Date of Patent: May 27, 2014

(54) COMPOSITION FOR ALLEVIATING ULTRAVIOLET RADIATION-INDUCED DAMAGE

(75) Inventors: Yutaka Ashida, Yokohama (JP); Yosuke Tojo, Yokohama (JP); Masashi Mita, Tokyo (JP); Chieko Mizumoto, Yokohama (JP); Shoichiro Shimada, Yokohama (JP); Kayo Matsumoto, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 34 days.

(21) Appl. No.: 13/138,786

(22) PCT Filed: Mar. 30, 2010

(86) PCT No.: PCT/JP2010/055648
§ 371 (c)(1),
(2), (4) Date: Feb. 16, 2012

(87) PCT Pub. No.: WO2010/113925
PCT Pub. Date: Oct. 7, 2010

(65) Prior Publication Data
US 2012/0142941 A1 Jun. 7, 2012

(30) Foreign Application Priority Data

Mar. 30, 2009 (JP) ................................. 2009-083077
Mar. 30, 2009 (JP) ................................. 2009-083078
Sep. 25, 2009 (JP) ................................. 2009-220983

(51) Int. Cl.
*A61K 31/401* (2006.01)

(52) U.S. Cl.
CPC .................................. *A61K 31/401* (2013.01)
USPC ....................................................... 514/428

(58) Field of Classification Search
CPC .................................................. A61K 31/401
USPC ....................................................... 514/428
See application file for complete search history.

(56) References Cited

U.S. PATENT DOCUMENTS

| | | | |
|---|---|---|---|
| 5,296,500 A | 3/1994 | Hillebrand | |
| 6,602,492 B2 | 8/2003 | Iwasaki et al. | |
| 6,703,031 B1 | 3/2004 | Iwasaki et al. | |
| 6,992,071 B2 | 1/2006 | Wondrak et al. | |
| 7,105,570 B2 | 9/2006 | Iwasaki et al. | |
| 7,226,937 B2 | 6/2007 | Wondrak et al. | |
| 2002/0115723 A1 | 8/2002 | Iwasaki et al. | |
| 2003/0194417 A1 | 10/2003 | Iwasaki et al. | |
| 2003/0223941 A1 | 12/2003 | Wondrak et al. | |
| 2005/0042188 A1 | 2/2005 | Wondrak et al. | |
| 2005/0130881 A1 | 6/2005 | Shashoua | |
| 2006/0009416 A1 | 1/2006 | Wondrak et al. | |
| 2009/0077676 A1 | 3/2009 | Hoeijmakers et al. | |

FOREIGN PATENT DOCUMENTS

| | | |
|---|---|---|
| JP | 11-286442 A | 10/1999 |
| JP | 2001-097888 A | 4/2001 |
| JP | 2002-047178 A | 2/2002 |
| JP | 2002-275079 A | 9/2002 |
| JP | 2005-515156 A | 5/2005 |
| JP | 2005-534625 A | 11/2005 |
| JP | 2005-343880 A | 12/2005 |
| JP | 2008-520200 A | 6/2008 |
| JP | 2008-185558 A | 8/2008 |
| RU | 94015599 A | 4/1996 |
| WO | WO 00/21925 A | 4/2000 |

OTHER PUBLICATIONS

Ahmed et al., "A new rapid and simple non-radioactive assay to monitor and determine the proliferation of lymphocytes: an alternative to [$^3$H]thymidine incoroporation assay," Journal of Immunological Methods, 1994, 170:211-224.

Fujinaga, Y., "Method for diagnosis of cataracts in adults," Cataract, Ophthalmology Mook, Mishima et al., Eds., Kanahara Co. Ltd., Tokyo, 1982, 17:10-17, with partial English translation of indicated portions, 2 pages.

Kajiro, Y., Ed., "Amino Acids," Harper's Biochemistry, $22^{nd}$ Edition, Maruzen Co. Ltd., Tokyo, Mar. 30, 1991, 21-30, with partial English translation of indicated portions, 2 pages.

Kinouchi et al., "D-Amino acid biosystem in mammal," Protein, Nucleic Acids and Enzymes, 2005, 50(5):453-460, with partial English translation of indicated portion, 1 page.

Maesato et al., "Cataract Model," Lens, Its Biochemical Mechanisms, S. Iwata, Ed., Medical-Aoi Publishing Co., Tokyo, Aug. 5, 1986, 318-323, with partial English translation of indicated portions, 2 pages.

Morikawa et al., "Alterations in D-amino acid levels in the brains of mice and rats after the administration of D-amino acids," Amino Acids, 2007, 32:13-20.

Nonaka, Shigeo, "Physiochemical Injury," Standard Dermatology, $7^{th}$ Edition, Arata et al., Eds., Igaku-Shoin Ltd., Tokyo, Mar. 15, 2004, Table of Contents and 98-99, with partial English translation of indicated portion, 2 pages.

Ohmori et al., "Physical Changes in Bovine Lens Homogenate Following Ultraviolet Irradiation and Their Prevention by Some Compounds," Chem. Pharm. Bull., 1985, 33(6):2432-2437.

Takigawa et al., Eds., "1. Photocontact dermatitis," Latest Methods for Treating Dermal Diseases, Nankodo Co., Ltd., Tokyo, Jan. 15, 2005, with partial English translation of indicated portions of pages, 3 pages.

Yamashina et al., "Amino Acids, Peptides, and Proteins," Principles of Biochemistry, $2^{nd}$ Ed., Hirokawa Publishing Co., Tokyo, Apr. 15, 1993, 132-147, with partial English translation of indicated portion, 1 page.

Zigman et al., "Sunlight and human cataracts," Invest. Ophthalmol. Vis. Sci., May 1979, 18(5):462-467.

Zhang et al., "Effects of N-acetylcysteine and glutathione ethyl ester drops on streptozotocin-induced diabetic cataract in rats," Molecular Vision, 2008, 14:862-870.

*Primary Examiner* — Robert Havlin

(74) *Attorney, Agent, or Firm* — Foley & Lardner LLP

(57) ABSTRACT

Disclosed are: a composition for alleviating ultraviolet irradiation-induced damage, which can be used on a daily based and is stable and safe; and a pharmaceutical preparation, a cosmetic and a food composition, each of which comprises the composition. The composition for alleviating ultraviolet irradiation-induced damage contains one or more compounds selected from the group consisting of D-glutamic acid, L-glutamic acid, D-proline, D-cystine, L-cystine, and derivatives and/or salts of the aforementioned compounds. The composition can be used as an external formulation for the skin, a cosmetic composition, an anti-wrinkle agent, a sunscreen agent, a pharmaceutical composition for treating and/or preventing skin diseases, a food composition, or a pharmaceutical composition for preventing or treating cataract.

13 Claims, 4 Drawing Sheets

COMPOSITION FOR ALLEVIATING ULTRAVIOLET RADIATION-INDUCED DAMAGE

CROSS-REFERENCE TO RELATED APPLICATIONS

This application is a National Stage application of PCT/JP2010/055648, filed Mar. 30, 2010, which claims priority from Japanese patent applications JP 2009-083077, filed Mar. 30, 2009; JP 2009-083078, filed Mar. 30, 2009; and JP 2009-220983, filed Sep. 25, 2009.

TECHNICAL FIELD

The present invention relates to a composition for alleviating an ultraviolet irradiation-induced damage comprising one or more compounds selected from the group consisting of D-glutamic acid, L-glutamic acid, D-proline, D-cysteine and L-cysteine and derivatives and/or salts thereof, a method for improving an ultraviolet radiation exposure-induced dermal disease and a dermal aesthetic condition comprising a step of administering one or more compounds selected from the group consisting of D-glutamic acid, L-glutamic acid, D-proline, D-cysteine and L-cysteine and derivatives and/or salts thereof, and a method for treating and/or preventing a cataract comprising a step of administering the compound described above.

BACKGROUND ART

Ultraviolet rays are classified into long wavelength region ultraviolet rays of longer than about 320 nm (UV-A), medium wavelength region ultraviolet rays of about 320 to about 280 nm (UV-B) and short wavelength region ultraviolet rays of shorter than about 280 nm (UV-C). Among these, the UV-C is not contained in solar lights reaching the ground since it is absorbed by ozone layers. The UV-A is not absorbed by the ozone layers and predominant in the ultraviolet rays reaching the ground. While the UV-B is partly absorbed by the ozone layers, it causes a skin damage at one-thousandth dose of the UV-A. Accordingly, both of the UV-A and the UV-B are important as major causes of the skin damages. Non-Patent Literature 1 discloses diseases in which the ultraviolet rays are implicated, including wrinkles, erythema, xeroderma pigmentosum, chronic actinic dermatitis, squamous cell carcinoma, basal cell carcinoma, malignant melanoma, Bowen disease, solar keratosis, photodermatosis, hydroa vacciniforme and photocontact dermatitis, while Non-Patent Literature 2 exemplifies solar dermatitis, chronic actinic dermatopathy, actinic keratosis, actinic cheilitis, Favre-Racouchot syndrome, photodermatosis, photocontact dermatitis, berloque dermatitis, photosensitive drug eruption, polymorphous light eruption, hydroa vacciniforme, solar urticaria, chronic photosensitive dermatitis, xeroderma pigmentosum, ephelides, porphyria, pellagra, Hartnup disease, solar keratosis, dermatomyositis, lichen planus, Darier disease, pityriasis rubra pilaris, rosacea, atopic dermatitis, chloasma, prurigo simplex and lupus erythematosus.

PRIOR ART DOCUMENTS

Non-Patent Documents

Non-Patent document 1: "HIHUSHIKKAN SAISHIN NO CHIRYO (Latest methods for treating dermal diseases)", 2005-2006 (Nankodo Co., Ltd.)

Non-Patent document 2: "HYOJUN HIHUKAGAKU (Standard dermatology)", 7th edition (Igaku-Shoin Ltd.)

DISCLOSURE OF THE INVENTION

Problem to be Solved by the Invention

Known conventional prophylactic and/or therapeutic agents for an ultraviolet irradiation-induced skin damage include an ultraviolet scattering agent which inhibits absorption of the ultraviolet by a skin, such as titanium oxide, an ultraviolet absorber, such as ethyl hexyl p-methoxycinnamic acid, or an antioxidant which removes a free radical generated by the ultraviolet. The ultraviolet scattering agent or the ultraviolet absorber is, however, not used everyday routinely although it is effective outdoor in preventing sunburn. The antioxidant is problematic in terms of stability and safety. In addition, known therapeutic agents for the ultraviolet irradiation-induced skin damages are limited only to symptomatic therapeutic agents. Accordingly, it is required to develop a prophylactic and/or therapeutic agent for an ultraviolet irradiation-induced skin damage which can routinely be used and which is stable and safe, as well as pharmaceutical, cosmetic and food products containing the same.

Means for Solving the Problem

The present invention provides a composition for alleviating an ultraviolet irradiation-induced damage comprising one or more compounds selected from the group consisting of D-glutamic acid, L-glutamic acid, D-proline, D-cysteine and L-cysteine and derivatives and/or salts thereof.

The composition for alleviating an ultraviolet irradiation-induced damage according to the invention may be applied as a skin formulation.

In the composition for alleviating an ultraviolet irradiation-induced damage according to the invention, the skin formulation described above may be used as a cosmetic product.

In the composition for alleviating an ultraviolet irradiation-induced damage according to the invention, the cosmetic product described above may be an anti-wrinkle agent.

In the composition for alleviating an ultraviolet irradiation-induced damage according to the invention, the cosmetic product described above may be a sunscreen agent.

In the composition for alleviating an ultraviolet irradiation-induced damage according to the invention, the cosmetic product described above may be used as a pharmaceutical product for a skin disease.

The skin disease described above may be selected from the group consisting of erythema, solar dermatitis, chronic actinic dermatopathy, actinic keratosis, actinic cheilitis, Favre-Racouchot disease, photodermatosis, photocontact dermatitis, berloque dermatitis, photosensitive drug eruption, polymorphous light eruption, hydroa vacciniforme, solar urticaria, chronic photosensitive dermatitis, xeroderma pigmentosum, ephelides, porphyria, pellagra, Hartnup disease, solar keratosis, dermatomyositis, lichen planus, Darier disease, pityriasis rubra pilaris, rosacea, atopic dermatitis, chloasma, prurigo simplex, lupus erythematosus, squamous cell carcinoma, basal cell carcinoma and Bowen disease.

In the composition for alleviating an ultraviolet irradiation-induced damage according to the invention, the pharmaceutical product for a skin disease described above may be a therapeutic agent for a skin disease.

In the composition for alleviating an ultraviolet irradiation-induced damage according to the invention, the pharmaceutical product for a skin disease described above may be a prophylactic agent for a skin disease.

The composition for alleviating an ultraviolet irradiation-induced damage according to the invention may be used as a food product.

The composition for alleviating an ultraviolet irradiation-induced damage according to the invention may be used as a pharmaceutical product for a cataract.

In the composition for alleviating an ultraviolet irradiation-induced damage according to the invention, the pharmaceutical product for a cataract described above may be a therapeutic or a prophylactic agent for a cataract.

The composition for alleviating an ultraviolet irradiation-induced damage according to the invention may be applied as an ophthalmic drop.

The cataract described above may be a senile cataract.

The present invention may provide a method for treating and/or preventing a skin disease caused by an ultraviolet radiation exposure comprising a step of administering a composition comprising one or more compounds selected from the group consisting of D-glutamic acid, L-glutamic acid, D-proline, D-cysteine and L-cysteine and derivatives and/or salts thereof. The skin disease described above may be selected from the group consisting of erythema, solar dermatitis, chronic actinic dermatopathy, actinic keratosis, actinic cheilitis, Favre-Racouchot disease, photodermatosis, photocontact dermatitis, berloque dermatitis, photosensitive drug eruption, polymorphous light eruption, hydroa vacciniforme, solar urticaria, chronic photosensitive dermatitis, xeroderma pigmentosum, ephelides, porphyria, pellagra, Hartnup disease, solar keratosis, dermatomyositis, lichen planus, Darier disease, pityriasis rubra pilaris, rosacea, atopic dermatitis, chloasma, prurigo simplex, lupus erythematosus, squamous cell carcinoma, basal cell carcinoma and Bowen disease.

The present invention may provide a method for improving a skin condition comprising a step of administering a composition comprising one or more compounds selected from the group consisting of D-glutamic acid, L-glutamic acid, D-proline, D-cysteine and L-cysteine and derivatives and/or salts thereof. In the method for improving a skin condition described above, the composition comprising one or more compounds selected from the group consisting of D-glutamic acid, L-glutamic acid, D-proline, D-cysteine and L-cysteine and derivatives and/or salts thereof may be a cosmetic composition or a food composition.

In the method for improving a dermal aesthetic condition according to the invention, the improvement of a dermal aesthetic condition includes, but is not limited to, an anti-wrinkle treatment and/or a sunscreen treatment.

The present invention may provide a method for treating and/or preventing a cataract comprising a step of administering a composition comprising one or more compounds selected from the group consisting of D-glutamic acid, L-glutamic acid, D-proline, D-cysteine and L-cysteine and derivatives and/or salts thereof.

In the method for treating and/or preventing a cataract according to the invention, the pharmaceutical product for a cataract described above may be an ophthalmic drop.

In the method for treating and/or preventing a cataract according to the invention, the cataract described above may be a senile cataract.

In the description, a "salt" means any salt including a metal salt, an amine salt and the like, provided that the alleviating effect on ultraviolet irradiation-induced damage of D-glutamic acid, L-glutamic acid, D-proline, D-cysteine and L-cysteine is not reduced. The metal salt described above may include an alkaline metal salt, an alkaline earth metal salt and the like. The amine salt described above may include a triethylamine salt, a benzylamine salt and the like.

As used herein, "derivative thereof" means D-glutamic acid, L-glutamic acid, D-proline, D-cysteine and L-cysteine each bound covalently at its amino group, carboxyl group or side chain with any substituent group, provided that the alleviating effect on ultraviolet irradiation-induced damage of D-glutamic acid, L-glutamic acid, D-proline, D-cysteine and L-cysteine is not reduced. The substituent group mentioned above includes, but is not limited to, a protective group, such as an N-phenylacetyl group, a 4,4'-dimethoxytrityl (DMT) group, etc.; a biological macromolecule, such as a protein, a peptide, a saccharide, a lipid, a nucleic acid, etc.; a synthetic polymer, such as a polystyrene, a polyethylene, a polyvinyl, a polyester, etc.; and a functional group such as an ester group, etc. The ester group mentioned above may include, for example, a methyl ester, an ethyl ester, other aliphatic ester or aromatic ester.

Since an amino acid can exist as an optical isomer which is an L-form or a D-form but a natural protein has L-amino acids bound via peptide bonds and only L-amino acids are employed excluding some exceptions such as a bacterial cell wall, it has been considered that in a mammal including a human only L-amino acids are present and utilized (Kinouchi, T. et al., TANPAKUSHITSU KAKUSAN KOSO (Proteins, nucleic acids and enzymes), 50:453-460 (2005), Lehninger Principles of Biochemistry [Vol. 1] 2nd ed., pp 132-147 (1993), Hirokawa Publishing Co., Harper's Biochemistry, Original version, 22nd ed., pp 21-30 (1991), Maruzen Co., Ltd.). Accordingly, only L-amino acids have mostly been employed as amino acids academically and industrially for a long time.

An exceptional case where a D-amino acid is employed may, for example, be a case of using as a starting material for an antibiotics produced by a microorganism and a case of a food additive employing a D-amino acid in a DL-amino acid mixture just for the purpose of reducing cost of fractionating only an L-amino acid from a mixture of the L-amino acid and the D-amino acid. Nevertheless, there has been no case of using a free or single body of D-amino acid industrially as a bioactive substance.

It was reported recently that D-serine and D-asparatic acid have bioactivities and that even in human a D-serine racemase is present and it was revealed that also in a mammal a D-amino acid is present in the body where it exerts a bioactivity. However, since entirely different bioactivities are observed between D-serine and L-serine as well as D-aspartic acid and L-aspartic acid in which the bioactivity is observed in a human, it is obvious that a D-amino acid should be handled as a substance which is different from an L-amino acid and the conventional findings with regard to amino acids should be understood as the findings with regard to L-amino acids.

As indicated in Examples described below, L-proline has no alleviating effect on ultraviolet irradiation-induced damage, and any alleviating effect on ultraviolet irradiation-induced damage of D-glutamic acid, L-glutamic acid, D-proline, D-cysteine and L-cysteine is not known so far. Accordingly, a composition for alleviating an ultraviolet irradiation-induced damage comprising one or more compounds selected from the group consisting of D-glutamic acid, L-glutamic acid, D-proline, D-cysteine and L-cysteine according to the invention is a novel invention.

Recently, it was reported that ddY mice were allowed to access a 10 mM aqueous solution of a D-amino acid for 2 weeks and then examined for the D-amino acid concentration in each organ, which was 3 to 1000 pmol per gland in a pineal body and 2 to 500 nmol per wet gram in a brain tissue (Morikawa, A. et al., Amino Acids, 32:13-20 (2007)). Based on this, the lower limit of daily intake of L- or D-glutamic acid, D-proline, L- or D-cysteine contained in a composition of the present invention was calculated.

As indicated in Examples described below, L- and D-glutamic acids of the present invention exhibit, even when given as a single body, an alleviating effect on ultraviolet irradiation-induced damage at a concentration ranging from 0.1 to 100 µM on cultured human keratinocyte and fibroblast. Accordingly, the amount of L- and/or D-glutamic acid contained in an composition of the present invention including pharmaceutical composition of the present invention, anti-wrinkle agent, sunscreen agent, cosmetic composition and food composition may vary in a wide range, provided that L- and/or D-glutamic acid as a single body is delivered to a keratinocyte or a fibroblast in an in vivo skin tissue at a concentration in the range specified above. When the composition of the present invention is a skin formulation, then the L- and/or D-glutamic acid content may range from 0.000015% by weight to 10% by weight in the total amount of the composition of the present invention, or to a maximum concentration by weight which is possible to be incorporated. Thus, when the composition of the present invention is a skin formulation, then the L- and/or D-glutamic acid content is preferably 0.00003% by weight to 0.3% by weight, most preferably 0.0003% by weight to 0.03% by weight. When the composition of the present invention is an internal formulation, the L- and/or D-glutamic acid content may be 0.00001% by weight to 100% by weight. When the composition of the present invention is an internal formulation, the L- and/or D-glutamic acid content is preferably 0.00002% by weight to 80% by weight, most preferably 0.0002% by weight to 60% by weight. The lower limit of the daily dose of D-glutamic acid contained in the composition of the present invention may be 0.01 ng, preferably 0.1 ng, more preferably 1 ng per kg body weight. The lower limit of the daily dose of L-glutamic acid contained in the composition of the present invention is less than a dose of a clinical drug (80 mg or more per kg body weight), and may be 0.1 mg, preferably 1 mg, more preferably 10 mg per kg body weight.

As indicated in Examples described below, D-proline of the invention exhibits, even when given as a single body, an alleviating effect on ultraviolet irradiation-induced damage at a concentration ranging from 0.01 to 1 µM on a cultured human fibroblast. Accordingly, the amount of D-proline contained in an pharmaceutical composition of the present invention, anti-wrinkle agent, sunscreen agent, cosmetic composition and food composition may vary in a wide range, provided that D-proline as a single body is delivered to a fibroblast in an in vivo skin tissue at a concentration in the range specified above. When the composition of the present invention is a skin formulation, then the D-proline content may range from 0.000015% by weight to 50% by weight in the total amount of the composition of the present invention, or to a maximum concentration by weight which is possible to be incorporated. Thus, when the composition is a skin formulation, then the D-proline content is preferably 0.00003% by weight to 30% by weight, most preferably 0.0003% by weight to 3% by weight. When the composition of the present invention is an internal formulation, the D-proline content may be 0.00001% by weight to 100% by weight. When the composition of the present invention is an internal formulation, the D-proline content is preferably 0.00002% by weight to 80% by weight, most preferably 0.0002% by weight to 60% by weight. The lower limit of the daily dose of D-proline contained in the composition of the present invention may be 0.01 ng, preferably 0.1 ng, more preferably 1 ng per kg body weight.

As indicated in Examples described below, L- and D-cysteines of the invention exhibit, even when given as a single body, an alleviating effect on ultraviolet irradiation-induced damage at a concentration ranging from 0.1 to 100 µM on cultured human keratinocyte and fibroblast. Accordingly, the amount of L- and/or D-cysteine contained in an composition of the present invention including pharmaceutical composition of the present invention, anti-wrinkle agent, sunscreen agent, cosmetic composition and food composition may vary in a wide range, provided that L- and/or D-cysteine as a single body is delivered to a keratinocyte or a fibroblast in an in vivo skin tissue at a concentration in the range specified above. When the composition of the present invention is a skin formulation, then the L- and/or D-cysteine content may range from 0.000015% by weight to 10% by weight in the total amount of the composition of the present invention, or to a maximum concentration by weight which is possible to be incorporated. Thus, when the composition of the present invention is a skin formulation, then the L- and/or D-cysteine content is preferably 0.00003% by weight to 0.3% by weight, most preferably 0.0003% by weight to 0.03% by weight. When the composition of the present invention is an internal formulation, the L- and/or D-cysteine content may be 0.00001% by weight to 100% by weight. When the composition of the present invention is an internal formulation, the L- and/or D-cysteine content is preferably 0.00002% by weight to 80% by weight, most preferably 0.0002% by weight to 60% by weight. The lower limit of the daily dose of D-cysteine contained in the composition of the present invention may be 0.01 ng, preferably 0.1 ng, more preferably 1 ng per kg body weight. The lower limit of the daily dose of L-cysteine contained in the composition of the present invention is less than a dose of a clinical drug (3 mg or more per kg body weight), and may be 0.01 mg, preferably 0.1 mg, more preferably 1 mg per kg body weight.

The pharmaceutical composition of the present invention may further comprise, in addition to one or more compounds selected from the group consisting of D-glutamic acid, L-glutamic acid, D-proline, D-cysteine and L-cysteine each as a single body, salts of D-glutamic acid, L-glutamic acid, D-proline, D-cysteine and L-cysteine, and derivatives capable of being subjected to in vivo drug metabolizing enzymes and the like whereby liberating D-glutamic acid, L-glutamic acid, D-proline, D-cysteine and L-cysteine, at least one pharmaceutically acceptable additive, provided that the alleviating effect on ultraviolet irradiation-induced damage of D-glutamic acid, L-glutamic acid, D-proline, D-cysteine and L-cysteine is not reduced. Such an additive includes, but is not limited to, a diluent, an extender, a binder, an adhesive, a lubricant, a glidant, a plasticizer, a disintegrant, a carrier solvent, a buffering agent, a colorant, a flavor, a sweetener, a preservative, a stabilizer, an adsorbent, as well as other pharmaceutical additives known to those skilled in the art.

An anti-wrinkle agent and/or a sunscreen agent of the invention can be prepared using only D-glutamic acid, L-glutamic acid, D-proline, D-cysteine and L-cysteine each as a single body, salts of D-glutamic acid, L-glutamic acid, D-proline, D-cysteine and L-cysteine, and derivatives capable of being subjected to in vivo drug metabolizing enzymes and the like whereby liberating D-glutamic acid, L-glutamic acid, D-proline, D-cysteine and L-cysteine. However, other components employed in skin formulations such as cosmetic and pharmaceutical products including quasi drugs may appropriately be incorporated as required to the extent that the effect of the invention is not reduced. Such other components (optionally incorporated components) include, for example, oils, surfactants, powders, colorants, water, alcohols, thickening agents, chelating agents, silicones, antioxidants, UV absorbers, humectants, fragrances, various pharmaceutically effective components, preservatives, pH adjusters, neutralizing agents.

The skin formulation and the cosmetic composition of the present invention may be any of those employed conventionally in a skin formulation and a cosmetic composition, such as an ointment, a cream, an emulsion, a lotion, a pack, a bath salt and the like, and their dosage forms are not specified particularly.

The cosmetic composition of the present invention may appropriately contain other components employed in skin formulations, such as cosmetic and pharmaceutical products including quasi drugs, provided that the alleviating effect on ultraviolet irradiation-induced damage of D-glutamic acid, L-glutamic acid, D-proline, D-cysteine and L-cysteine is not reduced. Such other components (optionally incorporated components) include, for example, oils, surfactants, powders, colorants, water, alcohols, thickening agents, chelating agents, silicones, antioxidants, UV absorbers, humectants, fragrances, various pharmaceutically effective components, preservatives, pH adjusters, neutralizing agents.

The food composition of the present invention may further comprises, in addition to D-glutamic acid, L-glutamic acid, D-proline, D-cysteine and L-cysteine each as a single body, salts of D-glutamic acid, L-glutamic acid, D-proline, D-cysteine and L-cysteine, and/or derivatives capable of being subjected to in vivo drug metabolizing enzymes and the like whereby liberating D-glutamic acid, L-glutamic acid, D-proline, D-cysteine and L-cysteine, a food-industrially acceptable component, such as a seasoning, a colorant, a preservative, provided that the alleviating effect on ultraviolet irradiation-induced damage of D-glutamic acid, L-glutamic acid, D-proline, D-cysteine and L-cysteine is not reduced.

The food composition of the present invention may be any of those employed conventionally in a food composition, such as a beverage, a gummy candy, a candy, a tablet, to which it is not limited.

An exposure to an ultraviolet ray is considered to be one of the causes not only of a dermal disease but also of an ophthalmic disease such as a cataract. A prolonged exposure of mice to an ultraviolet ray was reported to cause a turbidity in an anterior cortex of a lens, whereby allowing a cataract model to be obtained experimentally (Maeda, T. and Iwata, S., "SUISHOTAI SONO SEIKAGAKUTEKI KIKO (Lens, its biochemical mechanisms), p. 318-323, Ed. by Iwata, S., Medical-Aoi Publishings, Inc., Tokyo (1986)). Also, one of the causes of a senile cataract is considered to be an ultraviolet ray (Fujinaga, Y., "HAKUNAISHO (cataract), GANKA (ophthalmology) MOOK No. 17", p. 10, Ed. by Mishima et al., Kanehara & Co., Ltd., Tokyo (1982)), and Zigman et al. conducted an epidemiological surveillance in Manila, Tampa and Rochester and reported that there was a correlation between the ultraviolet irradiation amount and the cataract incidence and the ultraviolet ray is a risk factor for the cataract (Zigman, S. et al., Invest. Ophthalmol. Visual Sci. 18:462-467 (1979)). Accordingly, these findings, combined with Examples described below, suggest that D-glutamic acid, L-glutamic acid, D-proline, D-cysteine and L-cysteine having an alleviating effect on ultraviolet irradiation-induced damage are effective in preventing or treating the cataract.

DESCRIPTION OF EMBODIMENTS

Examples of the present invention described below are intended only to exemplify the invention rather than to limit the scope thereof. The scope of the invention is limited only by the description in claims.

Example 1

Alleviating Effect on Ultraviolet Irradiation-Induced Damage of D-Glutamic Acid

Cell

The cell employed was a commercially available human neonatal epidermal keratinocyte (Cryo NHEK-Neo, Sanko-Junyaku Co., Ltd.). This cell was inoculated at $2 \times 10^5$ cells/mL to a commercially available culture dish of 35 mm in diameter coated with a type I collagen (COL1, Asahi Techno Glass Co., Ltd.), where it was cultured in a commercially available serum-free medium (Defined Keratinocyte-SFM, Gibco., hereinafter referred to as "ordinary medium 1"). This cell was cultured for 5 to 7 days in a 5% $CO_2$ and saturated water vapor atmosphere at 37° C. until confluent while replacing the medium every 2 days.

For examining the effect of adding glutamic acid before UV irradiation (hereinafter referred to as "pretreatment"), the culture medium was switched 24 hours before the irradiation to a medium supplemented with 0.1 to 100 μM L- or D-glutamic acid.

UV Irradiation

Before UV-B irradiation, the culture medium was replaced with 1 mL of PBS. The UV-B irradiation was conducted using a in-house made UV exposing device (two UV lamps, Toshiba Medical Supply Corporation, TOREX FL20S-E-30/DMR) by irradiating a UV ray of 280 nm to 320 nm at 75 $J/cm^2$ from 40 cm above a culture dish in a state where the lid of the respective culture dish was removed. The UV dose was measured using UV RADIOMETER UVR-3036/S (Topcon Corporation).

The cell thus irradiated with UV was returned to the ordinary medium 1 where it was cultured in a 5% $CO_2$ and saturated water vapor atmosphere at 37° C. for 21 hours. For examining the effect of adding glutamic acid after UV irradiation (hereinafter referred to as "posttreatment"), this 21-hour cultured medium was added with 0.1 to 100 μM L- or D-glutamic acid.

Cell Damage Quantification

Thereafter, the culture medium was supplemented with Alamar Blue (trade mark, Biosource International Inc.) at a final concentration of 10%, and its supernatant was examined for the fluorescent intensity 3 hours later with an excitation wavelength of 544 nm and a fluorescent wavelength of 590 nm as described by Ahmed S. A. et al. (J. Immunol. Method. 170, 211-224 (1994)) and in accordance with the manufacture's instruction.

Results

Figure 1:
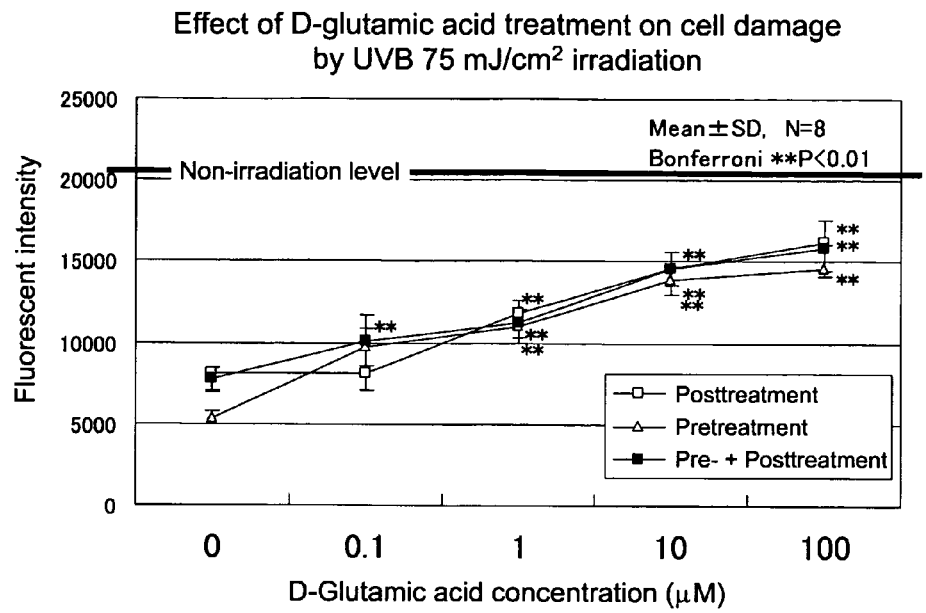
FIG. 1 is a graph showing the effect of a D-glutamic acid treatment in normal human epidermal keratinocytes.

FIG. 1 shows the results of the experiment investigating the effect of D-glutamic acid on the cell damage in keratinocytes induced by the ultraviolet irradiation with the UV-B at 75 mJ/cm$^2$. The error bars for relevant experimental conditions are the standard deviations of the measured values of the results of the experiments repeated eight times under identical conditions. The asterisk (**) indicates P<1% in Bonferroni test. The fluorescent intensity of Alamar Blue (trademark) in the absence of the UV irradiation was about 22,000, which was reduced to 5,000 to 7,000 when the cell damage occurred due to the UV-B irradiation. Nevertheless, when D-glutamic acid was added, the fluorescent intensity was increased, and the cell damage was alleviated. While this cell damage alleviating effect was observed regardless of the time of the D-glutamic acid treatment which was before or after the UV irradiation, a higher concentration of D-glutamic acid yielded a higher alleviating effect. No cell damage alleviating effect was observed when adding L-glutamic acid (data not shown). Based on the results described above, D-glutamic acid alleviates the UV-B-induced cell damage in keratinocytes in a concentration dependent manner.

Example 2

Alleviating Effect on Ultraviolet Irradiation-Induced Damage of D-Proline

Cell

The cell employed was a commercially available human neonatal dermal fibroblast (Cryo NHDF-Neo, Sanko-Junyaku Co., Ltd.). This cell was inoculated at 2×10$^5$ cells/mL to a commercially available culture dish of 35 mm in diameter (BD FALCON 353001, Beckton Dickinson Japan), where it was cultured in a commercially available cell culture medium (D-MEM (1 g/L glucose, Wako Pure Chemical Industries, Ltd.) supplemented with 10% fetal bovine serum (hereinafter referred to as "ordinary medium 2"). This cell was cultured for about 24 hours in a 5% CO$_2$ and saturated water vapor atmosphere at 37° C.

Thereafter, the culture medium for culturing the cell described above was switched to 1 mL of a BSO medium containing a glutathione biosynthesis inhibitor BSO (L-buthionine-(S,R)-sulfoximine, Wako Pure Chemical Industries, Ltd.) at 1×10$^{-3}$%, where the culture was conducted for about 24 hours in a 5% CO$_2$ and saturated water vapor atmosphere at 37° C. The BSO medium described above was prepared by a 200-fold dilution of a stock solution containing 0.2% BSO in ethyl alcohol with the ordinary medium 2 described above.

For examining the effect of adding proline before UV irradiation (hereinafter referred to as "pretreatment"), the culture medium was switched 24 hours before the irradiation to a medium supplemented with 0.1 µM L- or D-proline.

UV Irradiation Medium

Ferric chloride (II) was dissolved in a distilled water at 2×10$^{-3}$%, and the resultant solution was subjected to a 200-fold dilution (final concentration: 1×10$^{-5}$%) with a phosphate buffer solution PBS containing calcium ion and magnesium ion (PBS+) to obtain a medium (hereinafter referred to as "UV irradiation medium"), which was warmed preliminarily before use.

UV Irradiation

Before UV-A irradiation, the culture medium was replaced with 1 mL of the UV irradiation medium described above. The UV-A irradiation was conducted using a UV light uniform exposing device UVE-502S+EL-160 (SAN-EI ELECTRIC) by irradiating a UV ray of 320 nm to 400 nm at 15 J/cm$^2$ and 22.5 J/cm$^2$ from about 20 cm above a culture dish in a state where the lid of the respective culture dish was removed. The UV dose was measured using UV RADIOMETER UVR-3036/S (Topcon Corporation).

Treatment with Proline after UV Irradiation

After UV irradiation, the cell was returned to the ordinary medium 2 described above where it was cultured in a 5% CO$_2$ and saturated water vapor atmosphere at 37° C. for 21 hours. For examining the effect of adding proline after UV irradiation (hereinafter referred to as "posttreatment"), this 21-hour cultured medium was supplemented with 0.01 to 1000 µM L- or D-proline.

Quantification of Cell Damage Upon Posttreatment

Thereafter, the fluorescent intensity was measured by a method described in Example 1.

Results of Posttreatment

Figure 2:
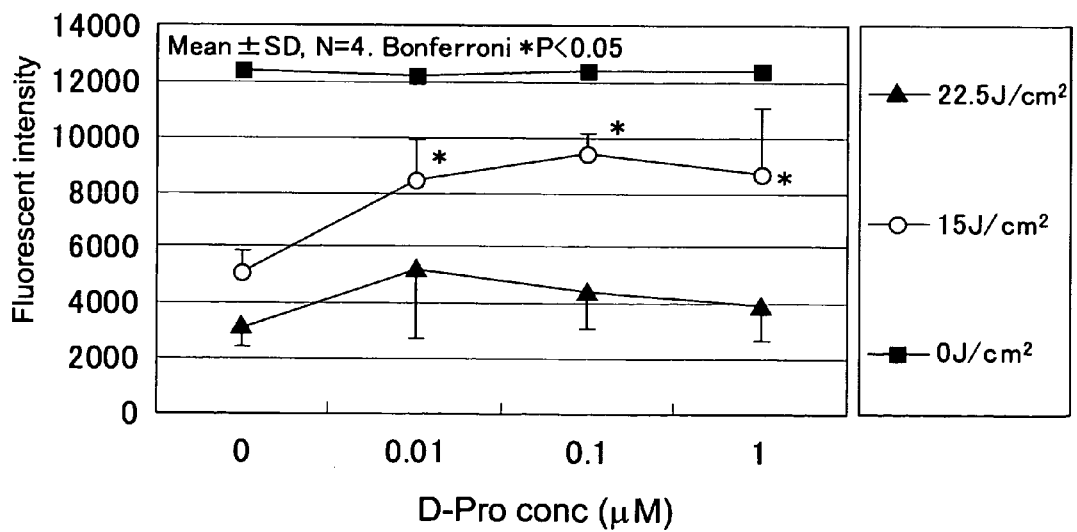
FIG. 2 is a graph showing the effect of a D-proline treatment after an ultraviolet irradiation in normal human dermal fibroblasts.

FIG. 2 shows the results of the experiment investigating the effect of D-proline on the cell damage in fibroblasts induced by the ultraviolet irradiation with the UV-A at 15 J/cm$^2$ and 22.5 J/cm$^2$. The error bars for relevant experimental conditions are the standard deviations of the measured values of the results of the experiments repeated four times under identical conditions. The asterisk (*) indicates p<5% in Bonferroni test. The fluorescent intensity of Alamar Blue (trademark) in the absence of the UV irradiation was about 12,000, which was reduced to about 5,000 when the cell damage occurred due to the UV-A irradiation at 15 J/cm$^2$. It was also reduced to about 3,000 when the cell damage occurred due to the UV-A irradiation at 22.5 J/cm$^2$. Nevertheless, when D-proline was added, the fluorescent intensity was increased, and the cell damage was alleviated.

Table 1 shows the results of the experiment investigating the effect of L- and D-proline on the cell damage in fibroblasts induced by the ultraviolet irradiation with the UV-A at 12.5 J/cm$^2$ and 15 J/cm$^2$. The error bars for relevant experimental conditions are the standard deviations of the measured values of the results of the experiments repeated four to six times under identical conditions. The asterisk (*) 1 shown here indicates p<0.1% when compared with a control and p=0.1% when compared with L-proline in Bonferroni test. The asterisk (*) 2 shown here indicates p<0.1% when compared with a control and p<5% when compared with L-proline in Bonferroni test. The fluorescent intensity of Alamar Blue (trademark) in the absence of the UV irradiation was about 12,000, which was reduced to about 2,500 and about 1,000 when the cell damage occurred due to the UV-A irradiation at 12.5 J/cm$^2$ and the UV-A irradiation at 15 J/cm$^2$, respectively. Almost no alleviation of the cell damage was noted when adding L-proline. Nevertheless, when D-proline was added, the fluorescent intensity was increased, and the cell damage was alleviated.

TABLE 1

| UV irradiation amount (J/cm$^2$) | Control | Fluorescent intensity D-proline (0.1 µM) | L-proline (0.1 µM) |
|---|---|---|---|
| 0 | 12380 ± 21 | 12270 ± 68 | 12211 ± 77 |
| 12.5 | 2503 ± 629 | 4615 ± 1218 *[1] | 2877 ± 834 |
| 15 | 1018 ± 89 | 2365 ± 648 *[2] | 1552 ± 320 |

Mean ± SD; N = 4-6 Bonferroni test
*[1] vs control P < 0.001, vs L-proline P < 0.001
*[2] vs control P < 0.001, vs L-proline P < 0.05

Quantification of Cell Damage Upon Pretreatment

The cell damage was quantified by detachment of the cell with a 0.25% trypsin-EDTA (Gibco) treatment for 5 minutes followed by centrifugation and washing, followed by a 0.2% trypan blue staining (Gibco) for verification of viability or death.

Results of Pretreatment

Figure 3:
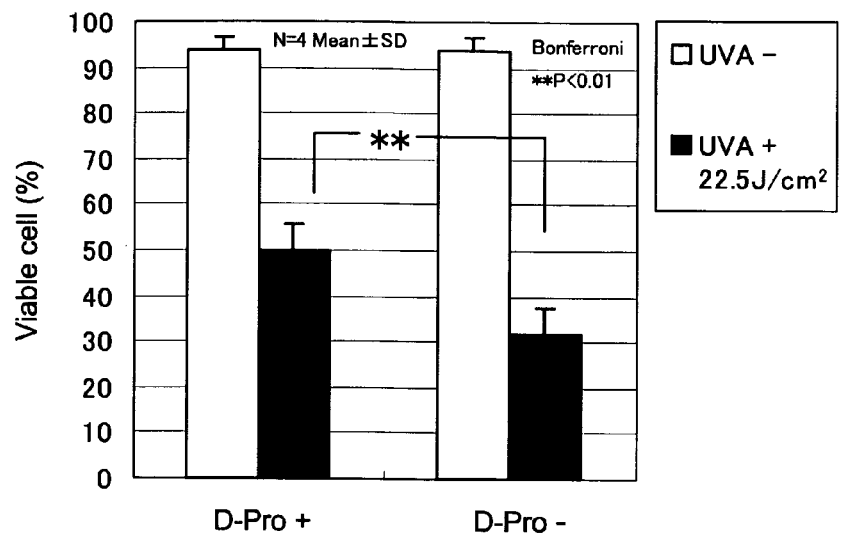
FIG. 3 is a graph showing the effect of a D-proline treatment before an ultraviolet irradiation in normal human dermal fibroblasts.

FIG. 3 shows the results of the experiment investigating the effect of D-proline on the cell damage in fibroblasts induced by the ultraviolet irradiation at 22.5 J/cm$^2$. The error bars for relevant experimental conditions are the standard deviations of the measured values of the results of the experiments repeated four times under identical conditions. The asterisk (**) indicates p<1% in Bonferroni test.

The percentage of the viable cell in the absence of the UV irradiation was about 95%, which was reduced to about 30% when the cell damage occurred due to the UV-A irradiation at 22.5 J/cm$^2$. Nevertheless, when D-proline was added, the percentage of the viable cell was increased to about 50%, and the cell death was alleviated. Based on the results described above, it was shown that the cell damage alleviating effect was independent of the time of the D-proline treatment, i.e., before or after the UV irradiation. Also it was shown that D-proline alleviates the UV-A-induced cell damage in a concentration dependent manner in the fibroblasts.

Example 3

Comparison of Alleviating Effect on Ultraviolet Irradiation-Induced Damage Between D-Proline and D-Glutamic Acid Methods The cell employed was a commercially available human neonatal dermal fibroblast (Cryo NHDF-Neo, Sanko-Junyaku Co., Ltd.), which was cultured by the same method described in Example 2. For examining the effect of adding D-proline or D-glutamic acid before UV irradiation, the culture medium was switched 24 hours before the irradiation to a medium supplemented with 0.1 µM D-proline or 1 µM L- or D-glutamic acid. The UV irradiation to a medium without such amino acids served as a control. The UV-A irradiation (22.5 J/cm$^2$) and the Alamar Blue (trade mark) cell damage quantification were conducted by the method described in Example 2.

Results

Figure 4:
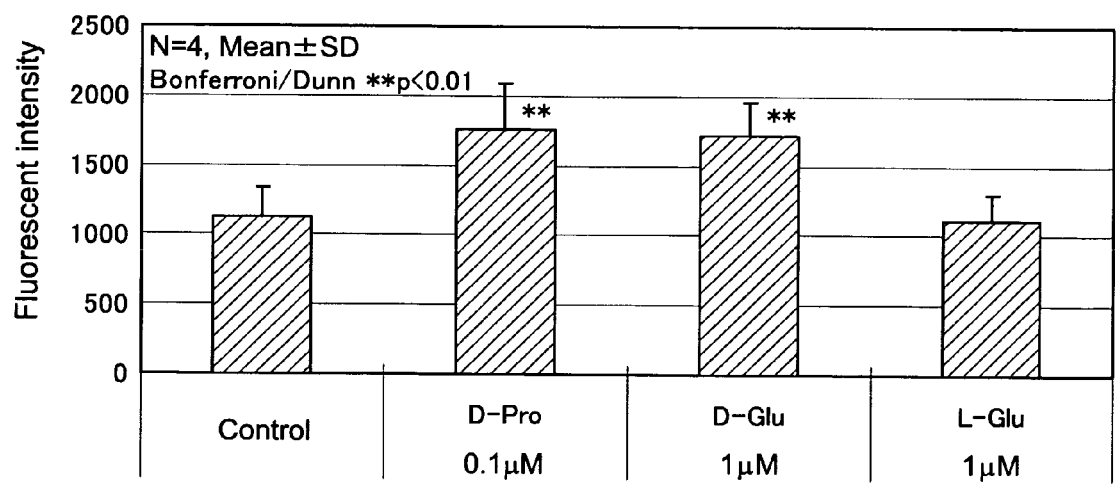
FIG. 4 is a graph showing the effect of a D-proline and glutamic acid treatment before an ultraviolet irradiation in normal human dermal fibroblasts.

FIG. 4 shows the results of the experiment investigating the effect of D-proline and L- or D-glutamic acid on the cell damage in fibroblasts induced by the UV-A irradiation at 22.5 J/cm$^2$. The error bars for relevant experimental conditions are the standard deviations of the measured values of the results of the experiments repeated four times under identical conditions. The asterisk (**) indicates p<1% in Bonferroni/Dunn test.

The fluorescent intensity was about 1,100 in the control. The fluorescent intensity in the presence of D-proline, L- or D-glutamic acid were about 1,750, about 1,100 or about 1,700, respectively. Based on these results, it was shown that D-proline and D-glutamic acid alleviate the UV-A-induced cell damage in the normal human dermal fibroblasts with a statistical significance. However, no cell damage alleviating effect was observed with L-glutamic acid. It was shown that D-proline alleviates the UV-induced cell damage at a concentration of one tenth when compared with D-glutamic acid.

Example 4

Alleviating Effect on Ultraviolet Irradiation-Induced Damage of L- and D-Cysteines Cell The cell employed was a commercially available human neonatal epidermal keratinocyte (Cryo NHEK-Neo, Sanko-Junyaku Co., Ltd.). This cell was inoculated at 1×10$^5$ cells/mL to a commercially available culture dish of 35 mm in diameter coated with a type I collagen (COL1, Asahi Techno Glass Co., Ltd.). This cell was cultured in a commercially available serum-free medium (Defined Keratinocyte-SFM, Gibco., hereinafter referred to as "ordinary medium 3") supplemented with a proliferator (Defined Keratinocyte-SFM Growth Supplement, Gibco) and antibiotics (PSF: penicillin, streptomycin and fungison) for 3 days in a 5% CO$_2$ and saturated water vapor atmosphere at 37° C. Thereafter, it was cultured for 2 days in 2 mL of the ordinary medium 3 containing 100 µM D-alanine, D-serine, D-hydroxyproline, D-aspartic acid, D-cysteine or L-cysteine. As a control, the ordinary medium 3 containing PBS instead of the D-amino acid was added to the ordinary medium 3.

UV Irradiation

Before UV-B irradiation, the culture medium was replaced with 1 mL of PBS. The UV-B irradiation was conducted using a in-house made UV exposing device (two UV lamps, Toshiba Medical Supply Corporation, TOREX FL20S-E-30/DMR) by irradiating a UV ray of 280 nm to 320 nm at 25 J/cm$^2$ from 40 cm above a culture dish in a state where the lid of the respective culture dish was removed. The UV dose was measured using UV RADIOMETER UVR-3036/S (Topcon Corporation).

The cell thus irradiated with UV was cultured in 900 µL of the ordinary medium 3 containing 100 µM D-alanine, D-serine, D-hydroxyproline, D-aspartic acid, D-cysteine or L-cysteine in a 5%, CO$_2$ and saturated water vapor atmosphere at 37° C. for 24 hours.

Quantification of Cell Damage

Thereafter, the fluorescent intensity was measured by the method described in Example 1.

Results

Figure 5:
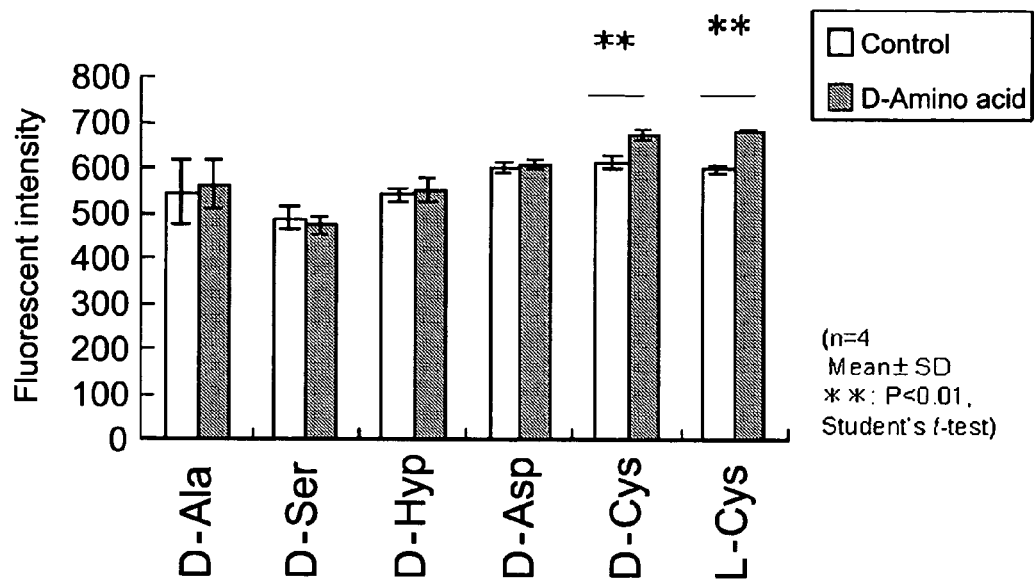
FIG. 5 is a graph showing the effect of a cysteine treatment in normal human epidermal keratinocytes.

FIG. 5 shows the results of the experiment investigating the effect of cysteine on the cell damage in keratinocytes induced by the ultraviolet irradiation with the UV-B at 25 mJ/cm$^2$. The error bars for relevant experimental conditions are the standard deviations of the measured values of the results of the experiments repeated four times under identical conditions. The asterisk (**) indicates p<1% in Student's t test. The fluorescent intensity of Alamar Blue (trademark) after occurrence of the cell damage due to the UV-B irradiation was about 570 in the presence of D-alanine, and was about 550 in the absence of D-alanine. The fluorescent intensity in the presence of D-serine was about 490 while the fluorescent intensity in the absence of D-serine was about 500. The fluorescent intensity in the presence of D-hydroxyproline was about 550 while the fluorescent intensity in the absence of D-hydroxyproline was about 550. The fluorescent intensity in the presence of D-aspartic acid was about 600 while the fluorescent intensity in the absence of D-aspartic acid was about 600. The fluorescent intensity in the presence of D-cysteine was about 700 while the fluorescent intensity in the absence of D-cysteine was about 600. The fluorescent intensity in the presence of L-cysteine was about 700 while the fluorescent intensity in the absence of L-cysteine was about 600. Based on these result, it was shown that cysteine, in both of L-form and D-form, alleviates the cell damage with a statistical significance.

Example 5

Alleviating Effect on Ultraviolet Irradiation-Induced Damage in XP Cells

Methods

A human dermal fibroblast derived from a patient having xeroderma pigmentosum (Group A) (XP30S (SVT), hereinafter referred to as "XP cell") which was obtained from Japan Health Science Foundation was employed and cultured by the same method described in Example 3. The pretreatment with 0.1 μM L- or D-glutamic acid, proline and cysteine and the quantification of the cell damage were conducted according to the methods described in Example 3. The UV-A irradiation was conducted using a UV light uniform exposing device UVE-502S+EL-160 (SAN-EI ELECTRIC) by irradiating a UV ray of 320 nm to 400 nm at 1 J/cm$^2$ from about 20 cm above a culture dish in a state where the lid of the respective culture dish was removed. The UV dose was measured using UV RADIOMETER UVR-3036/S (Topcon Corporation).

Results of L- and D-Glutamic Acids

Figure 6:
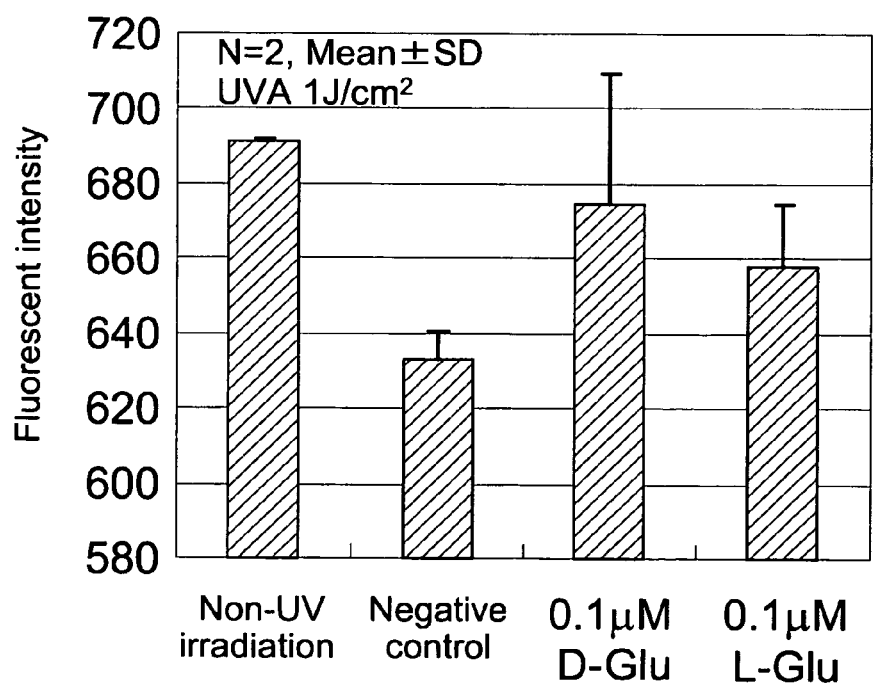
FIG. 6 is a graph showing the effect of an L- and D-glutamic acid treatment in XP cells.

FIG. 6 shows the results of the experiment investigating the effect of L- or D-glutamic acids on the cell damage in fibroblasts induced by the UV irradiation. The error bars for relevant experimental conditions are the standard deviations of the measured values of the results of the experiments repeated two times under identical conditions.

The fluorescent intensity was about 690 under the condition without UV irradiation in the absence of amino acid (hereinafter referred to as "non-UV irradiating condition") and was about 630 under the condition with UV irradiation in the absence of amino acid (hereinafter referred to as "negative control"). The fluorescent intensity in the presence of 0.1 μM of L- or D-glutamic acid was about 658 or about 675, respectively. Based on these results, it was shown that both of L- and D-glutamic acid alleviate the UV-A induced cell damage in XP cells.

Results of L- and D-Prolines

Figure 7:
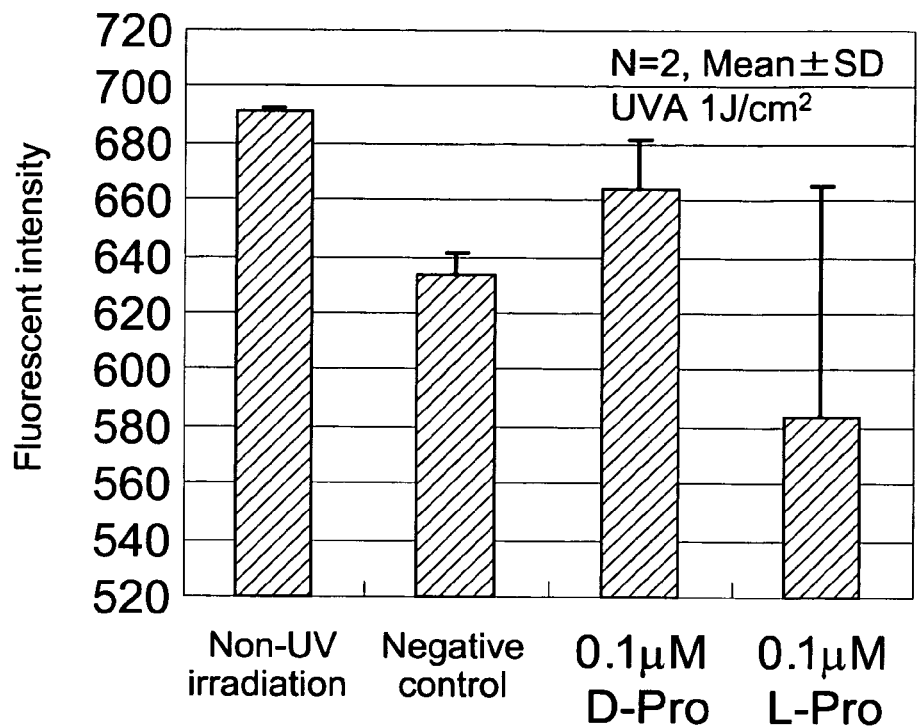
FIG. 7 is a graph showing the effect of an L- and D-proline treatment in XP cells.

FIG. 7 shows the results of the experiment investigating the effect of L- or D-proline on the cell damage in fibroblasts induced by the UV irradiation. The error bars for relevant experimental conditions are the standard deviations of the measured values of the results of the experiments repeated two times under identical conditions.

The fluorescent intensity was about 690 under the non-UV irradiating condition and was about 630 in the negative control. The fluorescent intensity in the presence of 0.1 μM of L- or D-proline was about 583 or about 664, respectively. Based on these results, it was shown that D-proline alleviates the UV-A induced cell damage in XP cells.

Results of L- and D-Cysteines

Figure 8:
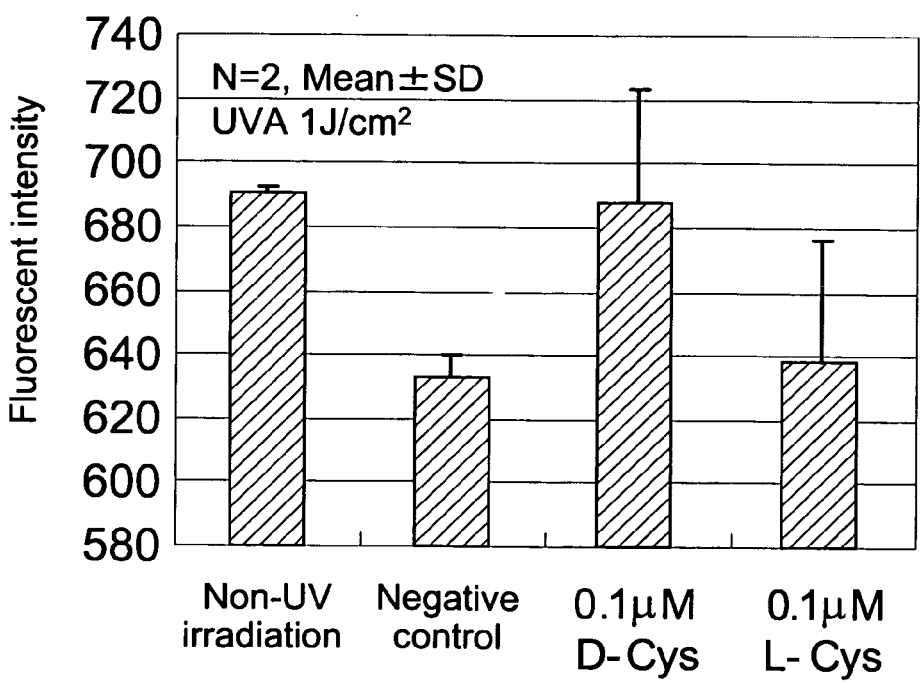
FIG. 8 is a graph showing the effect of an L- and D-cysteine treatment in XP cells.

FIG. 8 shows the results of the experiment investigating the effect of L- or D-cysteine on the cell damage in fibroblasts induced by the DV irradiation. The error bars for relevant experimental conditions are the standard deviations of the measured values of the results of the experiments repeated two times under identical conditions.

The fluorescent intensity was about 690 under the non-UV irradiating condition and was about 630 in the negative control. The fluorescent intensity in the presence of 0.1 μM of L- or D-cysteine was about 688 or about 638, respectively. Based on these results, it was shown that both of L- and D-cysteines alleviate the LTV-A induced cell damage in XP cells.

Based on the present invention, the formulation examples of an emulsion formulation, a patch formulation, a tablet, a soft capsule, a granule, beverage, a candy, a cookie, miso paste, a French dressing, a mayonnaise, a French bread, a soy sauce, yogurt, dried seasoning powder for rice, seasoning sauce/sauce for natto (Japanese fermented soybean paste), natto, unrefined black vinegar, cream, body cream, a gel formulation, a peel-off mask, a wet pack, an emulsion, a face lotion and an aerosol formulation comprising one or more compounds selected from the group consisting of D-glutamic acid, L-glutamic acid, D-proline, D-cysteine and L-cysteine are shown below. These formulation examples are listed only for the purpose of exemplification and not intended to restrict the scope of the invention.

Formulation Example 1

Emulsion Formulation

| (Composition) | Content (% by weight) |
|---|---|
| L- or D-glutamic acid, D-proline, or L- or D-cysteine | 0.42 |
| Behenyl alcohol | 0.2 |
| Cetanol | 0.5 |
| Glycerin mono fatty acid ester | 1.8 |
| Hardened castor oil POE (60) | 1.0 |
| White petrolatum | 2.0 |
| Liquid paraffin | 10.0 |
| Isopropyl myristate | 3.0 |
| Methyl polysiloxane (6 cs) | 1.5 |
| Conc. glycerin | 13.0 |
| Dipropylene glycol | 2.0 |
| Carboxyvinyl polymer | 0.25 |
| Sodium hyaluronate | 0.005 |
| Potassium hydroxide | As appropriate |
| Lactic acid | As appropriate |
| Sodium edetate | As appropriate |
| Ethylparaben | As appropriate |
| Purified water | Remainder |
| | 100.00 |

Formulation Example 2

Patch Formulation

| (Composition) | Content (% by weight) |
|---|---|
| L- or D-glutamic acid, D-proline, L- or D-cysteine | 0.3 |
| Polyacrylic acid | 3.0 |
| Sodium polyacrylate | 2.5 |
| Gelatin | 0.5 |
| Sodium carboxymethyl cellulose | 4.0 |
| Polyvinyl alcohol | 0.3 |
| Conc. Glycerin | 14.0 |
| 1,3-Butylene glycol | 12.0 |
| Aluminum hydroxide | 0.1 |
| Sodium edetate | 0.03 |
| Methylparaben | 0.1 |
| Purified water | Remainder |
| | 100.00 |

Formulation Example 3

Tablet

| (Composition) | Content (mg/tablet) |
|---|---|
| L- or D-glutamic acid, D-proline, or L- or D-cysteine | 360.5 |
| Lactose | 102.4 |
| Carboxymethyl cellulose calcium | 29.9 |
| Hydroxypropyl cellulose | 6.8 |
| Magnesium stearate | 5.2 |
| Crystalline cellulose | 10.2 |
| | 515.0 |

Formulation Example 4

Tablet

| (Composition) | Content (mg/tablet) |
|---|---|
| Sucrose ester | 70 |
| Crystalline cellulose | 74 |
| Methyl cellulose | 36 |
| Glycerin | 25 |
| L- or D-glutamic acid, D-proline, or L- or D-cysteine | 475 |
| N-Acetylglucosamine | 200 |
| Hyaluronic acid | 150 |
| Vitamin E | 30 |
| Vitamin B6 | 20 |
| Vitamin B2 | 10 |
| α-Lipoic acid | 20 |
| Coenzyme Q10 | 40 |
| Ceramide (Konnyaku extract) | 50 |
| L-proline | 300 |
| | 1500 |

Formulation Example 5

Soft Capsule

| (Composition) | Content (mg/capsule) |
|---|---|
| Edible soybean oil | 530 |
| Chinese Gutta Percha extract | 50 |
| Carrot extract | 50 |
| L- or D-glutamic acid, D-proline, or L- or D-cysteine | 100 |
| Royal jelly | 50 |
| Maca | 30 |
| GABA | 30 |
| Beeswax | 60 |
| Gelatin | 375 |
| Glycerin | 120 |
| Glycerin fatty acid ester | 105 |
| | 1500 |

Formulation Example 6

Soft Capsule

| (Composition) | Content (mg/capsule) |
|---|---|
| Brown rice germ oil | 659 |
| L- or D-glutamic acid, D-proline, or L- or D-cysteine | 500 |
| Resveratrol | 1 |
| Lotus germ extract | 100 |
| Elastin | 180 |
| DNA | 30 |
| Folic acid | 30 |
| | 1500 |

Formulation Example 7

Granule

| (Composition) | Content (mg/pack) |
|---|---|
| L- or D-glutamic acid, D-proline, or L- or D-cysteine | 400 |
| Vitamin C | 100 |
| Soybean isoflavon | 250 |
| Reduced lactose | 300 |
| Soybean oligosaccharide | 36 |
| Erythritol | 36 |
| Dextrin | 30 |
| Flavor | 24 |
| Citric acid | 24 |
| | 1200 |

Formulation Example 8

Beverage

| (Composition) | Content (g/60 mL) |
|---|---|
| Chinese Gutta Percha extract | 1.6 |
| Carrot extract | 1.6 |
| L- or D-glutamic acid, D-proline, or L- or D-cysteine | 1.6 |
| Reduced maltose syrup | 28 |
| Erythritol | 8 |
| Citric acid | 2 |
| Flavor | 1.3 |
| N-Acetylglucosamine | 1 |
| Sodium hyaluronate | 0.5 |
| Vitamin E | 0.3 |
| Vitamin B6 | 0.2 |
| Vitamin B2 | 0.1 |
| α-Lipoic acid | 0.2 |
| Coenzyme Q10 | 1.2 |
| Ceramide (Konnyaku extract) | 0.4 |
| L-proline | 2 |
| Purified water | Remainder |
| | 60 |

Formulation Example 9

Candy

| (Composition) | Content (% by weight) |
|---|---|
| Sugar | 50 |
| Syrup | 48 |
| L- or D-glutamic acid, D-proline, or L- or D-cysteine | 1 |
| Flavor | 1 |
|  | 100 |

Formulation Example 10

Cookie

| (Composition) | Content (% by weight) |
|---|---|
| Weak flour | 45.0 |
| Butter | 17.5 |
| Granulated sugar | 20.0 |
| L- or D-glutamic acid, D-proline, or L- or D-cysteine | 4.0 |
| Egg | 12.5 |
| Flavor | 1.0 |
|  | 100.0 |

Method for Producing Formulation Example 10 (Cookie)

Granular sugar is added in portions to butter while stirring, to which an egg and a flavor together with sodium L- or D-glutamate, D-proline or L- or D-cysteine are added and stirred. After mixing thoroughly, uniformly sieved weak flour is added and stirred, and allowed to stand as a bulk in a refrigerator. Thereafter, it is molded and baked for 15 minutes at 170° C. to obtain a cookie.

Formulation Example 11

Miso Seasoning Paste

| (Composition) | Content (g) |
|---|---|
| Soybean | 1000 |
| Malted rice | 1000 |
| Salt | 420 |
| L- or D-glutamic acid, D-proline, or L- or D-cysteine | 158 |
| Water | Remainder |
|  | 4000 |

Method for Producing Formulation Example 11 (Miso Seasoning Paste)

Malted rice is mixed thoroughly with a salt. Washed soybeans are soaked in 3 times its volumes of water, which are then drained off, and new water is added while boiling, and poured into a colander to collect the broth (tanemizu fluid), to which L- or D-glutamic acid, D-proline or L- or D-cysteine is dissolved at 10% w/v. The boiled beans are minced immediately, combined with malted rice mixed with salt, to which the tanemizu fluid described above containing L- or D-glutamic acid, D-proline or L- or D-cysteine dissolved therein is added and kneaded evenly to obtain a clay-like hardness. Dumplings are made and stuffed in a container compactly without forming any void, and the surface of the content is smoothened and sealed with a plastic film. After 3 months, the content is transferred to a new container and the surface is smoothened and sealed with a plastic film. Instead of adding L- or D-glutamic acid, D-proline or L- or D-cysteine to the tanemizu fluid, a malted rice producing a large amount of L- or D-glutamic acid, D-proline or L- or D-cysteine may be employed. Such malted rice can be selected by quantifying L- or D-glutamic acid, D-proline or L- or D-cysteine by the method described in Japanese Patent Unexamined Publication No. 2008-185558. Alternatively, a commercially available miso seasoning paste can be supplemented with D-glutamic acid, L-glutamic acid, D-proline, D-cysteine or L-cysteine or a salt thereof.

Formulation Example 12

French Dressing

| (Composition) | Content (g) |
|---|---|
| Salad oil | 27.0 |
| Vinegar | 30.0 |
| Sodium chloride | 0.9 |
| L- or D-glutamic acid, D-proline, or L- or D-cysteine | 1.1 |
| Pepper | 1.0 |
|  | 60.0 |

Method for Producing Formulation Example 12 (French Dressing)

Vinegar is combined with sodium chloride as well as L- or D-glutamic acid, D-proline or L- or D-cysteine, stirred thoroughly and then a pepper is added.

Formulation Example 13

Mayonnaise

| (Composition) | Content (g) |
|---|---|
| Salad oil | 134.0 |
| Vinegar | 5 |
| Sodium chloride | 0.9 |
| L- or D-glutamic acid, D-proline, or L- or D-cysteine | 1 |
| Egg yolk | 18 |
| Sugar | 0.2 |
| Pepper | 0.9 |
|  | 160.0 |

Method for Producing Formulation Example 13 (Mayonnaise)

An egg yolk (room temperature) is combined with vinegar, sodium chloride and pepper as well as L- or D-glutamic acid, D-proline or L- or D-cysteine, and stirred thoroughly using a whipping apparatus. Stirring is continued while adding salad oil in portions to form an emulsion. Finally, a sugar is added and the mixture is stirred.

Formulation Example 14

French Bread

| (Composition) | Content (g) |
|---|---|
| Extra-strength flour | 140 |
| Weak flour | 60 |
| Sodium chloride | 3 |
| Sugar | 6 |
| L- or D-glutamic acid, D-proline, or L- or D-cysteine | 2 |
| Dry yeast | 4 |
| Warm water | 128 |
| | 343 |

Method for Producing Formulation Example 14 (French Bread)

Warm water is combined with 1 g of sugar and dry yeast, which is then allowed to undergo a pre-fermentation. Extra-strength flour, weak flour, sodium chloride and 5 g of sugar are placed in a bowl together with L- or D-glutamic acid, D-proline or L- or D-cysteine, into which the pre-fermented yeast is placed. After kneading thoroughly into a ball-like dough, a primary fermentation is conducted at 30° C. The dough is kneaded again and allowed to stand, and then shaped into suitable forms, which are subjected to a final fermentation using an electronic fermentation machine. After forming coupes, baking is conducted for 30 minutes in an oven at 220° C.

Formulation Example 15

Soy Sauce

| (Composition) | Content (g) |
|---|---|
| Commercially available soy sauce | 990 |
| L- or D-glutamic acid, L- or D-cysteine | 10 |
| | 1000 |

Formulation Example 16

Soy Sauce

| (Composition) | Content (g) |
|---|---|
| Commercially available soy sauce | 900 |
| D-proline | 100 |
| | 1000 |

Method for Producing Formulation Examples 15 and 16 (Soy Sauce)

Commercially available soy sauce is supplemented with sodium L- or D-glutamate, D-proline or L- or D-cysteine, and stirred thoroughly. Instead of adding sodium L- or D-glutamate, D-proline or L- or D-cysteine or a salt thereof, malted rice producing a large amount of sodium L- or D-glutamate, D-proline or L- or D-cysteine may be employed for fermenting soy sauce. Such malted rice can be selected by quantifying sodium L- or D-glutamate, D-proline or L- or D-cysteine by the method described in Japanese Patent Unexamined Publication No. 2008-185558. Alternatively, commercially available soy sauce can be supplemented with sodium D-glutamate, sodium L-glutamate, D-proline, D-cysteine or L-cysteine or a salt thereof.

Formulation Example 17

Yogurt

| (Composition) | Content (g) |
|---|---|
| Milk | 880 |
| L. bulgaricus | 50 |
| S. thermophilus | 50 |
| L- or D-glutamic acid, D-proline, or L- or D-cysteine | 20 |
| | 1000 |

Method for Producing Formulation Example 17 (Yogurt)

Fermentation is conducted at 40° C. to 45° C. Other commercially available fermentation seed organisms may be employed and commercially available yogurt may be supplemented with sodium L- or D-glutamate, D-proline or L- or D-cysteine. Instead of adding sodium L- or D-glutamate, D-proline or L- or D-cysteine or a salt thereof, a seed organism producing a large amount of sodium L- or D-glutamate, D-proline or L- or D-cysteine may be employed for fermentation. Such an organism can be selected by quantifying sodium L- or D-glutamate, D-proline or L- or D-cysteine by the method described in Japanese Patent Unexamined Publication No. 2008-185558. Alternatively, commercially available yogurt can be supplemented with sodium D-glutamate, sodium L-glutamate, D-proline, D-cysteine or L-cysteine or a salt thereof.

Formulation Example 18

Dried Seasoning Powder for Rice

| (Composition) | Content (g) |
|---|---|
| L- or D-glutamic acid, D-proline, or L- or D-cysteine | 50 |
| Laver | 15 |
| Sodium L-glutamate | 10 |
| Sodium chloride | 2 |
| Roasted sesame | 10 |
| Dried mackerel shavings | 10 |
| Sugar | 1 |
| Soy sauce | 2 |
| | 100 |

Formulation Example 19

Seasoning, Sauce for Natto

| (Composition) | Content (g) |
|---|---|
| Commercially available sauce for natto | 9.9 |
| L- or D-glutamic acid, L- or D-cysteine | 0.1 |
| | 10 |

Formulation Example 20

Seasoning, Sauce for Natto

| (Composition) | Content (g) |
|---|---|
| Commercially available sauce for natto | 9 |
| D-proline | 1 |
| | 10 |

Formulation Example 21

Natto

| (Composition) | Content (g) |
|---|---|
| Commercially available natto | 19.9 |
| L- or D-glutamic acid, D-proline, or L- or D-cysteine | 0.1 |
| | 20 |

Method for Producing Formulation Example 21 (Natto)

Commercially available natto is supplemented with sodium L- or D-glutamate, D-proline or L- or D-cysteine, and stirred thoroughly. Instead of adding sodium L- or D-glutamate, D-proline or L- or D-cysteine or a salt thereof, an organism producing a large amount of sodium L- or D-glutamate, D-proline or L- or D-cysteine may be employed for producing natto. Such an organism can be selected by quantifying sodium L- or D-glutamate, D-proline or L- or D-cysteine by the method described in Japanese Patent Unexamined Publication No. 2008-185558. Alternatively, commercially available natto can be supplemented with sodium D-glutamate, sodium L-glutamate, D-proline, D-cysteine or L-cysteine or a salt thereof.

Formulation Example 22

Unrefined Black Vinegar

| (Composition) | Content (g) |
|---|---|
| Commercially available unrefined black vinegar | 950 |
| L- or D-glutamic acid, L- or D-cysteine | 50 |
| | 1000 |

Formulation Example 23

Unrefined Black Vinegar

| (Composition) | Content (g) |
|---|---|
| Commercially available unrefined black vinegar | 900 |
| D-proline | 100 |
| | 1000 |

Method for Producing Formulation Examples 22 and 23 (Unrefined Black Vinegar)

Commercially available unrefined black vinegar is supplemented with L- or D-glutamic acid, D-proline or L- or D-cysteine, and stirred thoroughly. Instead of adding L- or D-glutamic acid, D-proline or L- or D-cysteine or a salt thereof, an organism producing a large amount of L- or D-glutamic acid, D-proline or L- or D-cysteine may be employed for producing vinegar, black vinegar or unrefined vinegar. Such an organism can be selected by quantifying L- or D-glutamic acid, D-proline or L- or D-cysteine by the method described in Japanese Patent Unexamined Publication No. 2008-185558. Alternatively, commercially available unrefined black vinegar can be supplemented with sodium D-glutamate, sodium L-glutamate, D-proline, D-cysteine or L-cysteine or a salt thereof.

Formulation Example 24

Cream

| (Composition) | Content (%) |
|---|---|
| Liquid paraffin | 3 |
| Petrolatum | 1 |
| Dimethyl polysiloxane | 1 |
| Stearyl alcohol | 1.8 |
| Behenyl alcohol | 1.6 |
| Glycerin | 8 |
| Dipropylene glycol | 5 |
| Macadamia nut oil | 2 |
| Hardened oil | 3 |
| Squalane | 6 |
| Stearic acid | 2 |

-continued

| (Composition) | Content (%) |
|---|---|
| Cholesteryl hydroxystearate | 0.5 |
| Cetyl 2-ethylhexanoate | 4 |
| Polyoxyethylene hardened castor oil | 0.5 |
| Self-emulsified glycerin monostearate | 3 |
| Potassium hydroxide | 0.15 |
| Sodium hexametaphosphate | 0.05 |
| Trimethyl glycine | 2 |
| Potassium α-Tocopherol 2-L-ascirbic acid phosphoric acid diester | 1 |
| Tocopherol acetate | 0.1 |
| L- or D-glutamic acid, D-proline or L- or D-cysteine | 4 |
| Paraben | As appropriate |
| Trisodium edetate | 0.05 |
| 4-t-Butyl-4'-methoxy-benzoyl methane | 0.05 |
| Glyceryl diparamethoxycinnamate mono-2-ethylhexanoate | 0.05 |
| Colorant | As appropriate |
| Carboxyvinyl polymer | 0.05 |
| Purified water | Remainder |
| | 100.00 |

Formulation Example 25

Body Cream

| (Composition) | Content (%) |
|---|---|
| Dimethyl polysiloxane | 3 |
| Decamethyl cyclopentasiloxane | 13 |
| Dodecamethyl cyclohexasiloxane | 12 |
| Polyoxyethylene - methyl polysiloxane copolymer | 1 |
| Ethanol | 2 |
| Isopropanol | 1 |
| Glycerin | 3 |
| Dipropylene glycol | 5 |
| Polyethylene glycol 6000 | 5 |
| Sodium hexametaphosphate | 0.05 |
| Tocopherol acetate | 0.1 |
| L- or D-glutamic acid, D-proline or L- or D-cysteine | 5 |
| Fennel extract | 0.1 |
| Witch hazel extract | 0.1 |
| Carrot extract | 0.1 |
| L-Menthol p-oxybenzoate | |
| Trisodium edetate | 0.05 |
| Dimorpholinopyridazinone | 0.01 |
| Methylbis(trimethylsiolxy)silyl-isopentyl trimethoxycinnamate | 0.1 |
| Iron oxide yellow | As appropriate |
| Cobalt titanate | As appropriate |
| Dimethyl distearyl ammonium hectolite | 1.5 |
| Polyvinyl alcohol | 0.1 |
| Hydroxyethyl cellulose | 0.1 |
| Trimethylsiloxy silicic acid | 2 |
| Fragrance | As appropriate |
| Purified water | Remainder |
| | 100.00 |

Formulation Example 26

Gel Formulation

| (Composition) | Content (%) |
|---|---|
| Dimethyl polysiloxane | 5 |
| Glycerin | 2 |
| 1,3-Butylene glycol | 5 |
| Polyethylene glycol 1500 | 3 |
| Polyethylene glycol 20000 | 3 |
| Cetyl octanoate | 3 |
| Citric acid | 0.01 |
| Sodium citrate | 0.1 |
| Sodium hexametaphosphate | 0.1 |
| Dipotassium glycyrrhizinate | 0.1 |
| L- or D-glutamic acid, D-proline or L- or D-cysteine | 2 |
| Tocopherol acetate | 0.1 |
| Scutellaria root extract | 0.1 |
| Strawberry begonia extract | 0.1 |
| Trisodium edetate | 0.1 |
| Xanthane gum | 0.3 |
| Alkyl acrylate - methacrylate copolymer (Pemulen TR-2) | 0.05 |
| Agar powder | 1.5 |
| Phenoxyethanol | As appropriate |
| Dibutylhydroxytoluene | As appropriate |
| Purified water | Remainder |
| | 100.00 |

Formulation Example 27

Peel-Off Mask

| (Composition) | Content (%) |
|---|---|
| Ethanol | 10 |
| 1,3-Butylene glycol | 6 |
| Polyethylene glycol 4000 | 2 |
| Olive oil | 1 |
| Macadamia nut oil | 1 |
| Phytosteryl hydroxystearic acid | 0.05 |
| Lactic acid | 0.05 |
| Sodium lactate | 0.1 |
| Disodium L-ascorbate sulfate | 0.1 |
| Potassium α-Tocopherol 2-L-ascirbic acid phosphoric acid diester | 0.1 |
| L- or D-glutamic acid, D-proline or L- or D-cysteine | 10 |
| Fish collagen | 0.1 |
| Sodium chondroitin sulfate | 0.1 |
| Sodium carboxymethyl cellulose | 0.2 |
| Polyvinyl alcohol | 12 |
| p-oxybenzoate | As appropriate |
| Fragrance | As appropriate |
| Purified water | Remainder |
| | 100.00 |

Formulation Example 28

Wet Pack

| (Composition) | Content (%) |
|---|---|
| Glycerin | 1 |
| 1,3-Butylene glycol | 8 |
| Xylit | 2 |
| Polyethylene glycol 1500 | 2 |
| Rosemary oil | 0.01 |
| Sage oil | 0.1 |
| Citric acid | 0.02 |
| Sodium citrate | 0.08 |
| Sodium hexametaphosphate | 0.01 |
| Hydroxypropyl-β-cyclodextrin | 0.1 |
| L- or D-glutamic acid, D-proline or L- or D-cysteine | 0.5 |
| Birch extract | 0.1 |
| Lavender extract | 0.01 |
| Xanthane gum | 0.05 |
| Carboxyvinyl polymer | 0.15 |
| p-oxybenzoate | As appropriate |
| Purified water | Remainder |
|  | 100.00 |

Formulation Example 29

Emulsion

| (Composition) | Content (%) |
|---|---|
| Liquid paraffin | 7 |
| Petrolatum | 3 |
| Dexamethyl cyclopentasiloxane | 2 |
| Behenyl alcohol | 1.5 |
| Glycerin | 5 |
| Dipropylene glycol | 7 |
| Polyethylene glycol 1500 | 2 |
| Jojoba oil | 1 |
| Isostearic acid | 0.5 |
| Stearic acid | 0.5 |
| Behenic acid | 0.5 |
| Pentaerythritol tetra 2-ethylhexanoate | 3 |
| Cetyl 2-ethylhexanoate | 3 |
| Glycerin monostearate | 1 |
| Polyoxyethylene glycerin monostearate | 1 |
| Potassium hydroxide | 0.1 |
| Sodium hexametaphosphate | 0.05 |
| Stearyl glycyrrhizinate | 0.05 |
| L- or D-glutamic acid, D-proline or L- or D-cysteine | 1 |
| Royal jelly extract | 0.1 |
| Yeast extract | 0.1 |
| Tocopherol acetate | 0.1 |
| Acetylated sodium hyaluronate | 0.1 |
| Trisodium edetate | 0.05 |
| 4-t-Butyl-4'-methoxy-dibenzoylmethane | 0.1 |
| 2-Ethylhexyl paramethoxycinnamate | 0.1 |
| Carboxyvinyl polymer | 0.15 |
| Paraben | As appropriate |
| Fragrance | As appropriate |
| Purified water | Remainder |
|  | 100.00 |

Formulation Example 30

Emulsion

| (Composition) | Content (%) |
|---|---|
| Dimethylpolysiloxane | 2 |
| Behenyl alcohol | 1 |
| Batyl alcohol | 0.5 |
| Glycerin | 5 |
| 1,3-Butylene glycol | 7 |
| Erythritol | 2 |
| Hardened oil | 3 |
| Squalane | 6 |
| L- or D-glutamic acid, D-proline or L- or D-cysteine | 0.3 |
| Pentaerythritol tetra 2-ethylhexanoate | 2 |
| Polyoxyethylene glyceryl isostearate | 1 |
| Polyoxyethylene glyceryl monostearate | 1 |
| Potassium hydroxide | As appropriate |
| Sodium hexametaphosphate | 0.05 |
| Phenoxyethanol | As appropriate |
| Carboxyvinyl polymer | 0.1 |
| Purified water | Remainder |
|  | 100.00 |

Formulation Example 31

Face Lotion

| (Composition) | Content (%) |
|---|---|
| Ethyl alcohol | 5 |
| Glycerin | 1 |
| 1,3-Butylene glycol | 5 |
| Polyoxyethylene polyoxypropylene decyltetradecyl ether | 0.2 |
| Sodium hexametaphosphate | 0.03 |
| Trimethyl glycin | 1 |
| Sodium polyaspartic acid | 0.1 |
| Potassium α-Tocopherol 2-L-ascirbic acid phosphoric acid diester | 0.1 |
| Thiotaurine | 0.1 |
| L- or D-glutamic acid, D-proline or L- or D-cysteine | 8 |
| Trisodium EDTA | 0.1 |
| Carboxyvinyl polymer | 0.05 |
| Potassium hydroxide | 0.02 |
| Phenoxyethanol | As appropriate |
| Fragrance | As appropriate |
| Purified water | Remainder |
|  | 100.00 |

Formulation Example 32

Face Lotion

| (Composition) | Content (%) |
|---|---|
| Ethanol | 10 |
| Dipropylene glycol | 1 |
| Polyethylene glycol 1000 | 1 |
| Polyoxyethylene methyl glucoside | 1 |
| Jojoba oil | 0.01 |
| Glyceryl tri 2-ethylhexanoate | 0.1 |
| Polyoxyethylene hardened castor oil | 0.2 |
| Polyglyceryl diisostearate | 0.15 |
| Sodium N-stearoyl-L-glutamate | 0.1 |
| Citric acid | 0.05 |
| Sodium citrate | 0.2 |
| Potassium hydroxide | 0.4 |
| Dipotassium glycyrrhizinate | 0.1 |
| Arginine hydrochloride | 0.1 |
| L-Ascorbic acid 2-glucoside | 2 |
| L- or D-glutamic acid, D-proline or L- or D-cysteine | 0.5 |
| Trisodium edetate | 0.05 |
| 2-Ethylhexyl paramethoxycinnamate | 0.01 |
| Dibutylhydroxytoluene | As appropriate |
| Paraben | As appropriate |
| Deep seawater | 3 |
| Fragrance | As appropriate |
| Purified water | Remainder |
| | 100.00 |

Formulation Example 33

Aerosol Urea Skin Formulation Stock Solution

| (Composition) | Content (% by weight) |
|---|---|
| Ethanol | 15.0 |
| Polyoxyethylene hardened castor oil 50 | 1.5 |
| Diphenhydramine | 1.0 |
| Dibucaine | 2.0 |
| Tocopherol acetate | 0.5 |
| L- or D-glutamic acid, D-proline or L- or D-cysteine | 0.1 |
| Isostearic acid | 0.1 |
| 1,3-Butylene glycol | 3.0 |
| Polyethylene glycol 400 | 3.0 |
| Camphor | 0.05 |
| Urea | 20.0 |
| Purified water | Remainder |
| | 100.00 |

Formulation Example 34

Aerosol Urea Spray

| (Composition) | Content (% by weight) |
|---|---|
| Aerosol urea skin formulation stock solution | 65.0 |
| Dimethyl ether | 35.0 |
| | 100.00 |

Method for Filling Formulation Example 34 (Aerosol Urea Spray)

Aerosol urea skin formulation stock solution and dimethyl ether are charged in a pressure-resistant aluminum aerosol container whose inner surface is coated with Teflon (trade mark) to yield an aerosol formulation.

FIG. 1: (1) Effect of D-glutamic acid treatment on cell damage by UVB 75 mJ/cm$^2$ irradiation,
(2) Fluorescent intensity,
(3) Non-irradiation level,
(4) Posttreatment, Pretreatment, Pre-+Posttreatment
FIG. 2: (5) D-Glutamic acid concentration (μM)
FIG. 3: (6) Viable cell (%)
FIG. 4: (7) N=4, Means±SD,
(8) Control
FIG. 5: (9) Control, D-Amino acid
FIG. 6: (10) Non-UV irradiation,
(11) Negative control

The invention claimed is:

1. A method for alleviating an ultraviolet irradiation-induced damage after ultraviolet radiation, comprising administering, to a patient in need thereof, a composition comprising one or more compounds selected from the group consisting of D-proline, and derivatives and/or salts thereof.

2. The method according to claim 1, wherein the composition is a skin formulation.

3. The method according to claim 2, wherein the composition is a cosmetic product.

4. The method according to claim 3, wherein the composition is an anti-wrinkle agent.

5. The method according to claim 2, wherein the composition is a sunscreen agent.

6. The method according to claim 2, wherein the composition is a pharmaceutical product for a skin disease.

7. The method according to claim 6, wherein the skin disease is selected from the group consisting of erythema, solar dermatitis, chronic actinic dermatopathy, actinic keratosis, actinic cheilitis, Favre-Racouchot disease, photodermatosis, photocontact dermatitis, berloque dermatitis, photosensitive drug eruption, polymorphous light eruption, hydroa vacciniforme, solar urticaria, chronic photosensitive dermatitis, xeroderma pigmentosum, ephelides, porphyria, pellagra, Hartnup disease, solar keratosis, dermatomyositis, lichen planus, Darier disease, pityriasis rubra pilaris, rosacea, atopic dermatitis, chloasma, prurigo simplex, lupus erythematosus, squamous cell carcinoma, basal cell carcinoma and Bowen disease.

8. The method according to claim 6, wherein the pharmaceutical product for a skin disease is a therapeutic agent for a skin disease.

9. The method according to claim 6, wherein the pharmaceutical product for a skin disease is a prophylactic agent for a skin disease.

10. The method according to claim 1, wherein the composition is a food product.

11. The method according to claim 1, wherein the composition is a pharmaceutical product for a cataract.

12. The method according to claim 11, herein the pharmaceutical product for a cataract is a therapeutic agent for a cataract or a prophylactic agent for a cataract.

13. The method according to claim 11, wherein the composition is an ophthalmic drop.

* * * * *